United States Patent [19]
Mann

[11] Patent Number: 5,800,351
[45] Date of Patent: Sep. 1, 1998

[54] ELECTRODE SUPPORTING HEAD SET

[75] Inventor: Christopher Allen Mann, Granada Hills, Calif.

[73] Assignee: Rest Technologies, Inc., Northridge, Calif.

[21] Appl. No.: 725,768

[22] Filed: Oct. 4, 1996

[51] Int. Cl.$^6$ .................................................. A61B 5/0408
[52] U.S. Cl. ........................................ 600/383; 607/139
[58] Field of Search ................................ 600/383, 390, 600/544; 607/139

[56] References Cited

U.S. PATENT DOCUMENTS

| | | | |
|---|---|---|---|
| 3,490,439 | 1/1970 | Rolston | 600/383 |
| 3,998,213 | 12/1976 | Price | 600/383 |
| 4,537,198 | 8/1985 | Corbett | 128/639 |
| 4,709,702 | 12/1987 | Sherwin | 128/644 |
| 4,836,219 | 6/1989 | Hobson et al. | 128/782 |
| 4,928,696 | 5/1990 | Henderson et al. | 128/644 |
| 5,293,867 | 3/1994 | Oommen | 600/383 |
| 5,313,952 | 5/1994 | Hoch | 600/390 |
| 5,479,934 | 1/1996 | Imran | 128/139 |

*Primary Examiner*—Lee S. Cohen
*Attorney, Agent, or Firm*—Alan Davis; Louis Dachs

[57] ABSTRACT

The invention is a headset for holding electrodes on the head of a person for measuring the electrical activity of the person's brain. In detail, the invention includes a pair of fittings for attachment about the ears of a person. A first flexible front strap is adapted to fit about the forehead of the person is connected to each fitting. A second flexible strap adapted to fit about the rear of the head of the person is also connected to each fitting. A plurality of sets of flexible members is connected to each fitting and which are adapted to fit over the top portion of the head of the person between the first and second straps. A plurality of electrode mounts are movably mounted to each of the plurality of sets of guide members. The head set's ear fittings also provides a means for holding the lead wires of electrodes placed on a person's face for monitoring such parameters as eye movement and facial muscle activity during routine sleep testing.

22 Claims, 4 Drawing Sheets

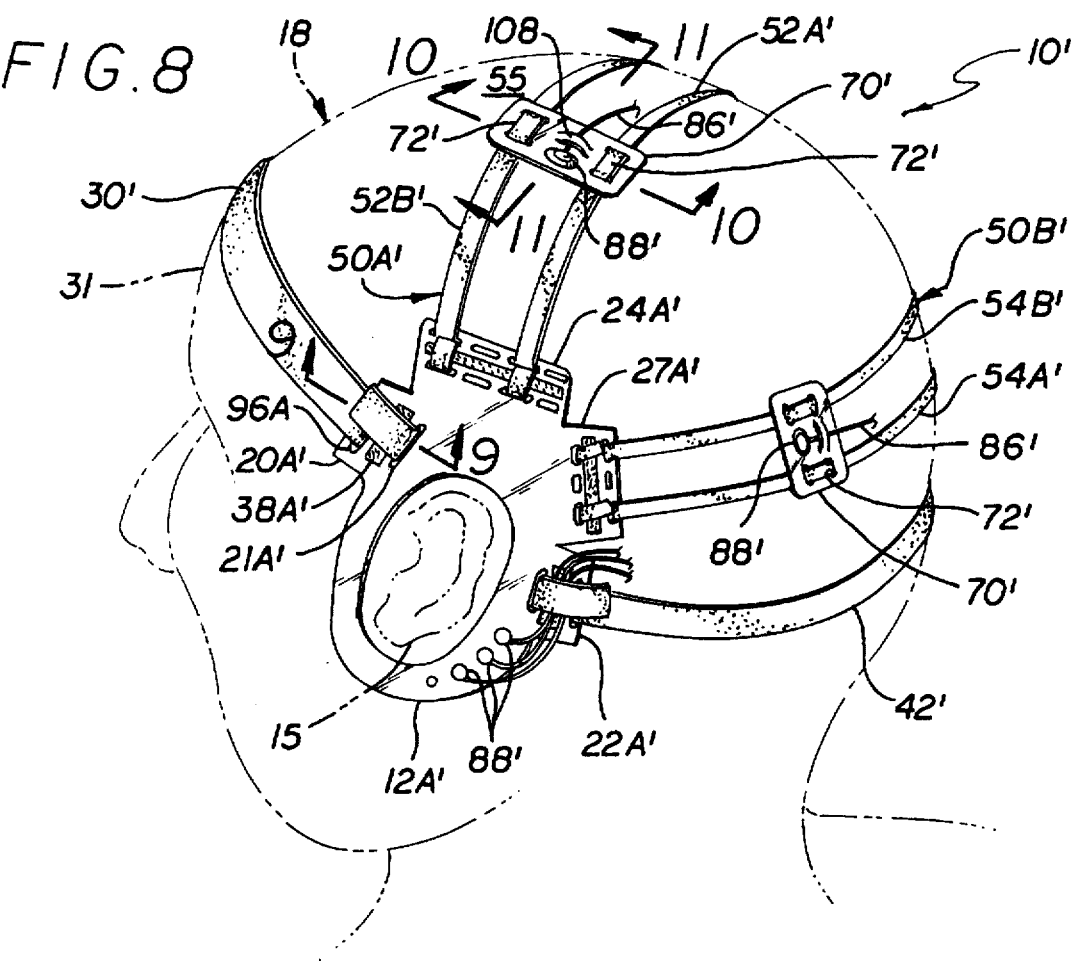
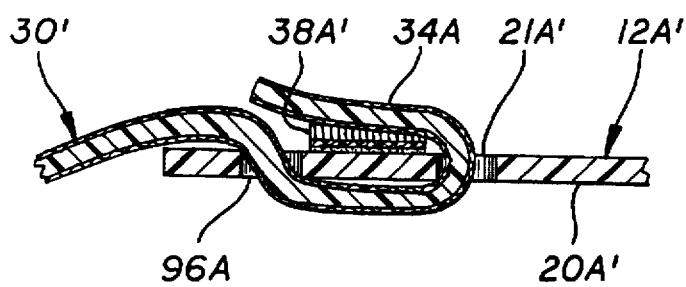
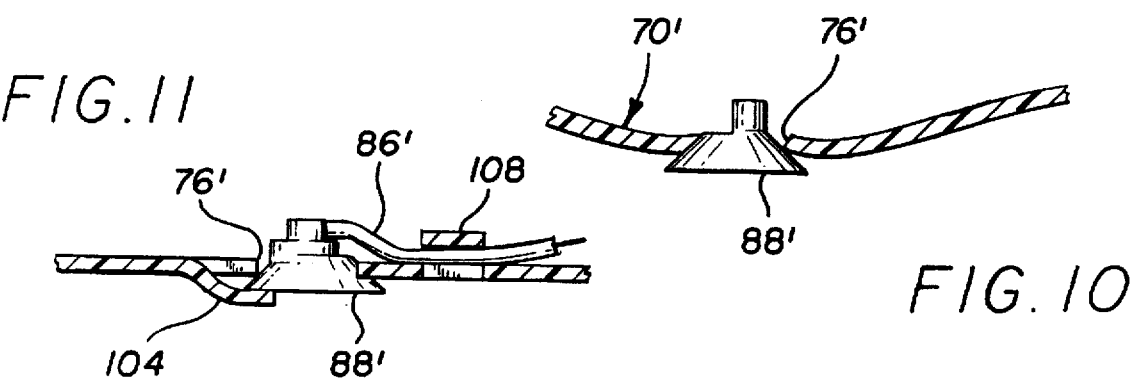

5,800,351

ELECTRODE SUPPORTING HEAD SET

BACKGROUND OF THE INVENTION

1. Field of the Invention

The invention relates to the field of head sets for supporting electrodes for connection to brain electrical activity monitoring apparatus and, in particular, to a head set that is adjustable so as to fit heads of different sizes and shapes and, also which incorporates means to adjust electrodes' positions on the head.

2. Description of Related Art

There are numerous head sets available for monitoring electrical activity of the brain of human beings, and, in particular, medical patients. For example, U.S. Pat. No. 5,478,934 "EEG Headpiece With Disposable Electrodes And Apparatus And System And Method For Use Therewith" by M. A. Imran discloses a "spider web" type head set that couples to a strap that extends about the chin and neck of the patent. While the straps are adjustable, there is no capability to adjust the webbing itself; thus it may not be comfortable for all persons. In addition, electrode position can not be significantly varied. Furthermore, because of its bulkiness and use of a chin restraint, it is unsuitable for monitoring a sleeping person during overnight sleep, especially when evaluating the sleeping person for a breathing disorder during sleep. In particular, chin straps necessarily affect jaw position and can influence breathing. This adversely effects sleep and thus must be avoided during sleep monitoring tests being carried on for medical evaluation of a patient.

Another example of a head set is disclosed in U.S. Pat. No. 4,928,696 "Electrode-Supporting Headset" by D. J. Henderson, et al. The Henderson, et al. design uses a metal wire frame to which are mounted adjustable length straps having electrodes mounted thereon. While providing for adjustment of the straps for a better fit and electrode placement on the patient's head, the metal wire frame would be uncomfortable for a person attempting to sleep. U.S. Pat. No. 4,537,196 "Electrode Cap" by S. Corbett discloses a cloth like skull cap that completely covers the head of the person. It is secured by straps to a belt assembly that fits about the upper torso of the patent. The main disadvantage of this design is that a snug fitting cap completely covering the head of the person could become hot after long periods of use. In addition, persons with long hair would also find it uncomfortable. Finally, there is no ability to adjust electrode position.

U.S. Pat. No. 4,709,702 "Electroencephalographic Cap" by G. W. Sherwin discloses several types of head sets. One is in the form of a skull cap completely covering the head. The second includes a horizontal strap that extends completely about the head with a second vertical strap that extends over the top of the head and which is connected at its ends to the horizontal strap. Electrodes are mounted on both the vertical and horizontal straps. The use of under-the-chin restraining straps make them unsuitable for sleep monitoring. U.S. Pat. No. 4,836,219 "Electronic Sleep Monitor Headgear" by J. A. Hobson, et al. also discloses a simple horizontal and vertical strap head set for mounting an eye monitoring sensor. However, there is no means for adjusting it to fit different size heads, nor, in fact, does the head set include means for mounting electrodes.

Thus, it is a primary object of the invention to provide a head set for mounting electrodes for monitoring brain electrical activity especially during sleep.

It is another primary object of the invention to provide a head set for mounting electrodes for monitoring brain electrical activity that is fully adjustable to accommodate different size heads.

It is a further object of the invention to provide a head set for mounting electrodes for monitoring brain electrical activity that allows for the adjusting of electrode placement.

It is a still further object of the invention to provide a head set for mounting electrodes for monitoring brain activity that does not require a supporting strap under or on the chin.

It is another object of the invention to provide a head set for mounting electrodes for monitoring brain electrical activity that requires only minimal coverage of the head of the person thus exposing most of the head.

It is another object of the invention to provide a head set for mounting electrodes for monitoring brain activity that is comfortable to wear for extended periods of time without hindering a person's sleep.

It is another object of the invention to provide a means for holding the lead wires of electrodes and other sensors placed on the head as part of a sleep monitoring procedure.

SUMMARY OF THE INVENTION

The invention is a head set for holding commercially available electrodes which measure the electrical activity of the brain of a person, most often a medical patient. In detail, the head set includes first and second mounting fittings for attachment about the ears of the person. A first flexible strap is adapted to fit about the forehead of the person and is connected by its ends to the first and second mounting fittings. A second flexible strap is adapted to fit about the rear of the head of the person and is also connected to the first and second mounting fittings. A plurality of sets of flexible guide members are also connected by their ends to the mounting fittings between the first and second straps and are adapted to fit over the top portion of the head of the person. Preferably, the guide members of each set are in a parallel spaced relationship with each other.

The first and second straps, as well as the pairs of flexible members, are adjustable in length. This is accomplished by having the ends of the straps and each of the guide members looped through individual openings in the first and second mounting fittings and back onto themselves, thus their length is determined by the amount of overlap. Fasteners, preferably, but not limited to, the form of hook and eye types (commercially sold under the trade name of VELCRO™) are used to secure the overlapped portions place.

A plurality of electrode mounts are movably mounted to each of the plurality of sets of semi-flexible guide members. The electrodes are removably mounted in the electrode mounts. The individual guide members are deformable in cross-sectional shape and pass through the "belt loops" in the guide members such that each of the guide members are deformed when passing therethrough. This deformation, as the guide member passes through the belt loop, produces sufficient friction so as to releasably hold the electrode mounts in any set position. Since all the electrodes have lead wires attached thereto for coupling to electrical recording apparatus, a flexible wire harness is detachably mounted to the rear strap to prevent them from becoming tangled. In addition, to insure that the electrodes remain in good contact with the head, the middle of the electrode mount can be formed into a shallow "U" shape with the electrode mounted in the bottom of the U. The electrode mount being semi-flexible, the U shaped portion acts as a spring to bias the electrode toward the head. In addition, different types of commercially available electrodes can also be mounted on the attachment fittings.

The novel features which are believed to be characteristic of the invention, both as to its organization and method of operation, together with further objects and advantages thereof, will be better understood from the following description in connection with the accompanying drawings in which the presently preferred embodiments of the invention are illustrated by way of example. It is to be expressly understood, however, that the drawings are for purposes of illustration and description only and are not intended as a definition of the limits of the invention.

BRIEF DESCRIPTION OF THE DRAWINGS

FIG. 3 is a partial cross-sectional view of the head set shown in FIG. 2, taken along the line 3—3 illustrating the construction of the front strap and the method of securing to the attachment fittings.

FIG. 8 is a partial side view of the head set shown in FIG. 2, illustrating a second embodiment of the head set.

FIG. 9 is a cross-sectional view of FIG. 8 taken along the line 9—9.

FIG. 10 is partial cross-sectional view of FIG. 8 taken along the line 10—10

FIG. 11 is a partial cross-sectional view of FIG. 8 taken along the line 11—11.

DESCRIPTION OF THE PREFERRED EMBODIMENT

Figure 1:
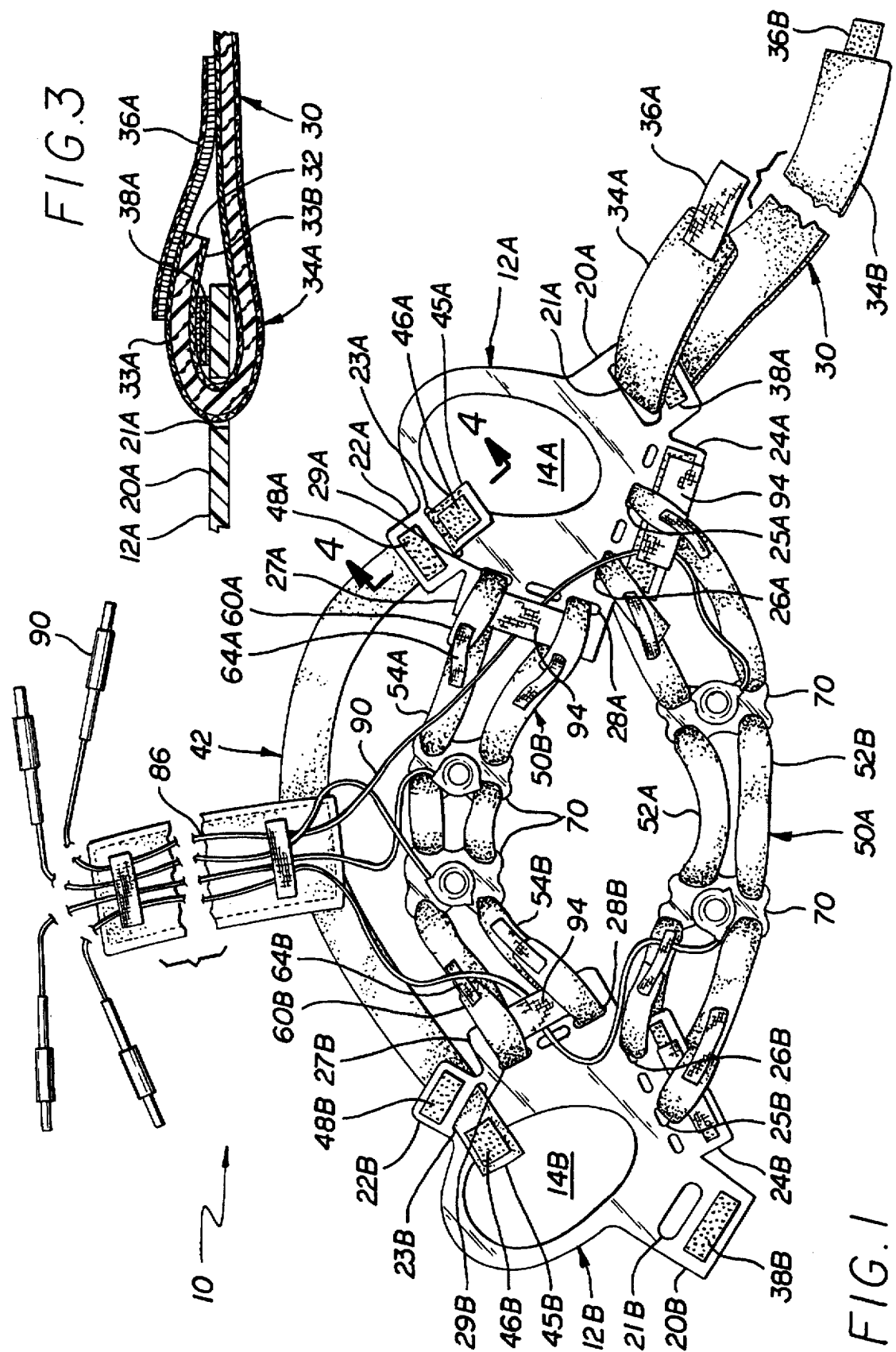
FIG. 1 is a top view of the head set flattened out.
Figure 2:
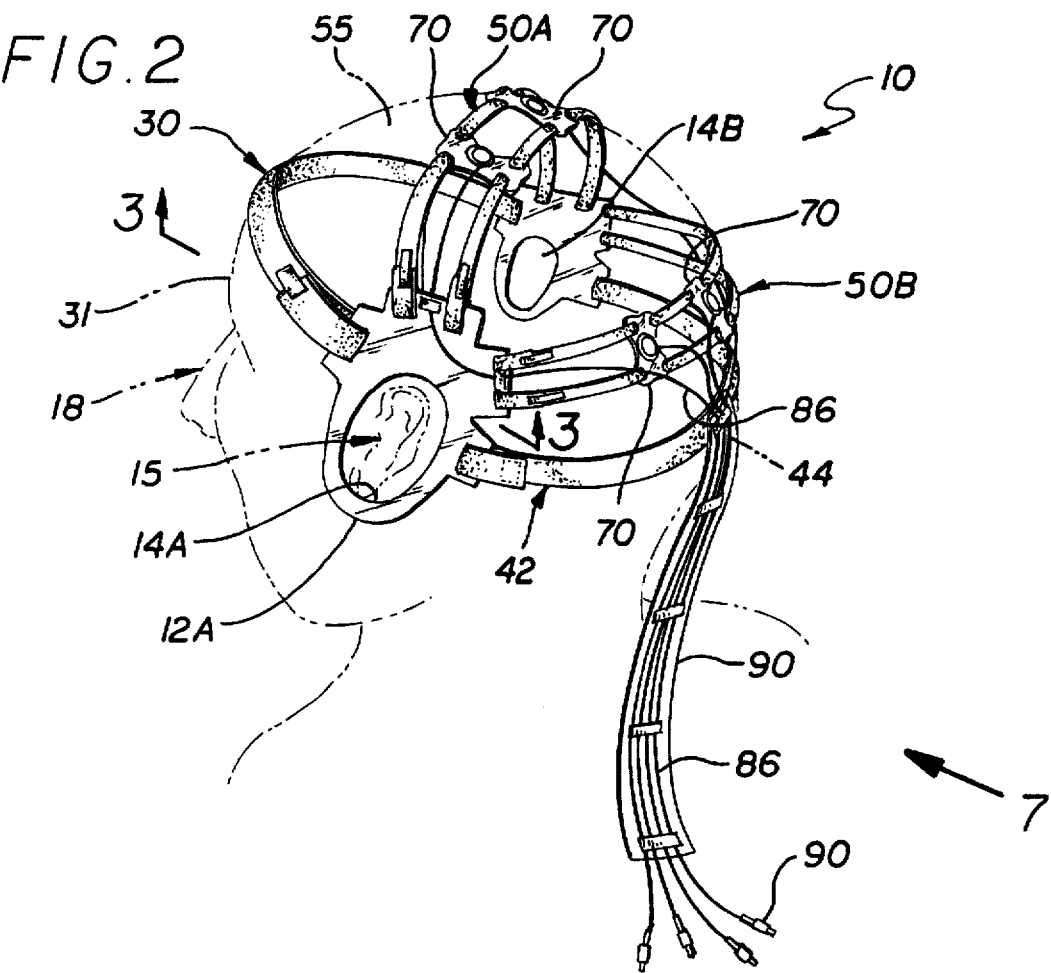
FIG. 2 is a perspective view of the head set mounted on the head of a person.

Referring to FIGS. 1 and 2, the head set, generally indicated by numeral 10, includes first and second ear attachment fittings 12A and 12B having ear openings 14A and 14B for fitting over the ears 15 of a persons head 18. Each of the fittings 12A and 12B incorporate a series of tabs: 20A and 20B that include slots 21A and 21B that extend therethrough; tabs 22A and 22B, that include slots 23A and 23B also extending therethrough. Each fitting 12A and 12B also include tabs 24A and 24B with slots 25A and 25B and slots 26A and 26B that extend therethrough. Finally, tabs 27A and 27B include slots 28A and 28B and slots 29A and 29B that extend therethrough. The fittings 12A and 12B are, preferably, made of a thin semi-stiff plastic material, such that they comfortably fit over the ear and will deform when the person's head 18 rests against a pillow while in bed. However they could be covered with padded cloth to provide a "softer feel".

Still referring to FIGS. 1 and 2 and additionally to FIG. 3, a first flexible and compressible strap 30, having a generally flat rectangular shape, is adapted to fit about the forehead 31 of the person's head 18. As particularly illustrated in FIG. 3, preferably, the strap 30 includes a flexible compressible foam core 32 bonded to cover sheets 33A and 33B made of cloth having a nap suitable as the eye portion of a hook and eye (VELCRO™) type fastener (hereinafter referred to as "eyes"). The strap 30 includes end portions 34A and 34B that are looped through slots 21A and 21B in the tabs 20A and 20B and back thereon. The end portions 34A and 34B include strips 36A and 36B that further include the hook portions of hook and eye type fasteners (hereinafter referred to as "hooks") thereon such that these strips can be joined to the cover sheet 33A of the strap 30. Thus the strap 30 can easily be adjusted to fit the head 18. In addition, pads 38A and 38B having hooks are bonded to the tabs 20A and 20B that act as additional securing means for the strap 30 upon engagement with cover sheet 33B.

Figure 4:
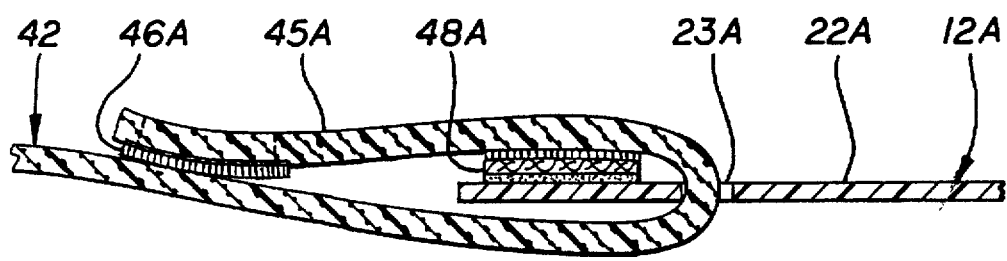
FIG. 4 is a view of the head set shown in FIG. 2, taken along the arrow 4 illustrating the method of securing the rear strap to the attachment fitting.

Still referring to FIGS. 1 and 2 and, additionally, to FIG. 4, a second flexible and compressible strap 42, similar in construction to strap 30 is adapted to fit about the rear 44 of the head 18 of the person. The strap 42 includes end portions 45A and 45B that are looped through slots 23A and 23B on tabs 22A and 22B and back thereon. Pads 46A and 46B mounted on the end portions 45A and 45B that incorporate hooks used to secure the strap 42. Additionally, pads 48A and 48B mounted on the tabs 22A and 22B include hooks providing additional securing means. Thus the strap 42 also is fully adjustable.

A pair of identical sets 50A and 50B of flexible and generally parallel members 52A and 52B, and 54A and 54B, respectively, extend over the top 55 of the head 18. They are also adjustably connected between the fittings 12A and 12B in a manner similar to similar to strap 30 and have similar construction thereto. Thus for example, member 54A, includes end portions 60A and 60B that are looped through slots 29A and 29B in the tabs 27A and 27B and back thereon and releasably secured thereto by strips 64A and 64B (similar to strips 36A and 36B and in a similar manner). Therefore, the member 54A can also be easily adjusted to fit the head 18. The other members 52A and 52B of set 50A and 54A of set 50B are identical in construction to member 54B. Thus member 52A is looped through slots 26A and 26B, member 52B is looped through slots 25A and 25B, and member 54B is looped through slots 28A and 28B. Of course, the number of sets of guide members is not limited to two, more could be included when determined to be necessary.

Figure 5:
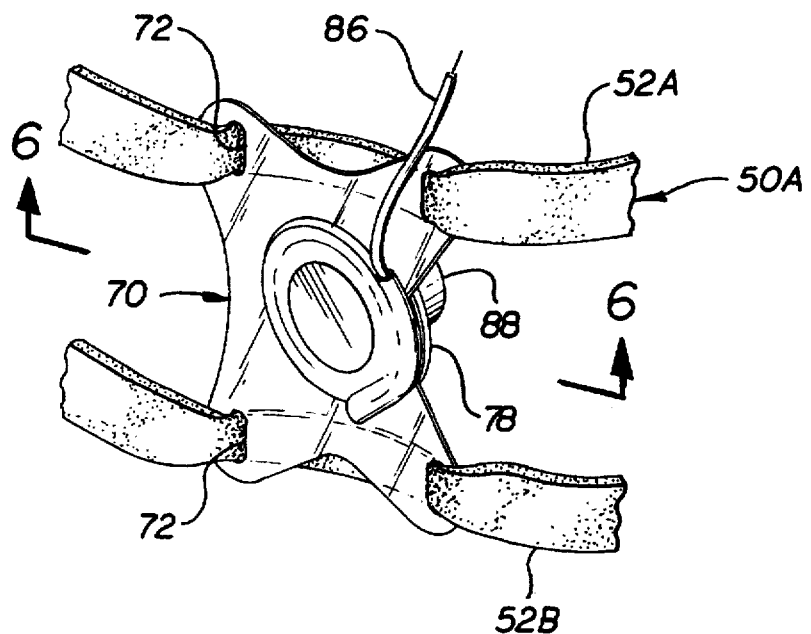
FIG. 5 is a enlarged perspective view of a portion of FIG. 2 illustrating the electrode mounts.
Figure 6:
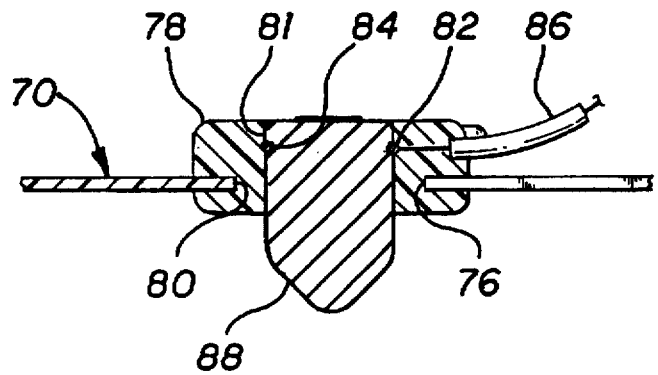
FIG. 6 is a cross-section view of FIG. 1 taken along the line 6—6 illustrating the details of the electrode mount.

Still referring to FIGS. 1 and 2, and additionally to FIGS. 5 and 6, a plurality of flexible electrode mounts 70 are movably mounted to each set 50A and 50B of guide members. The individual guide members 52A and 52B and 58A and 58B being deformable in cross-sectional shape pass through belt loops 72 on the electrode mounts 70 such that each of the guide members are deformed when passing therethrough. This deformation produces sufficient friction so as to releasably hold the electrode mounts 70 in any set position.

The electrode mounts 70 include a centrally located hole 76 in which is mounted a round insulation ring 78. The ring 78 includes an outer groove 80 that is engaged with the edge of the hole 76 and a centrally located electrode mounting hole 81. The electrode mounts 70 being flexible, it is an easy matter to push the rings 78 in place. The rings 78 also include a groove 82 in the inner edge of the hole 81 in which is mounted a electrical contact 84 that is coupled to a lead wire 86. An electrode 88, mounts in the hole 81 and makes electrical contact with contact 84. Suitable electrodes 88 and rings 78 are disclosed in the previously discussed U.S. Pat. No. 5,479,934 "EEG Headpiece With Disposable Electrodes And Apparatus And System And Method For Use Therewith" by M. A. Imran and are commercially available from Physiometrix, Inc. No. Billerica, Md. For example, a suitable contact 84 is Model No. 1500M and a suitable electrode is Model No. 1100.

Figure 7:
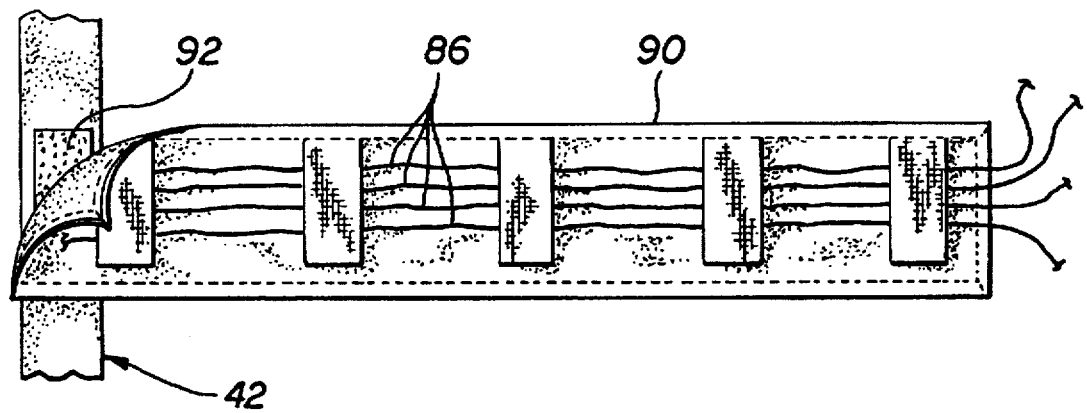
FIG. 7 is a section of FIG. 1 taken along the arrow 7 illustrating the wire harness releasably attached to the rear strap.

Referring to FIGS. 1, 2 and additionally to FIG. 7, the lead wires 86 are gathered together and extend into and through a wire harness 90 detachably mounted to the second flexible strap 42 by means of hook and eye type fasteners 92. To prevent the lead wires from moving about when the person tosses or turns in bed, hook and eye type fastener assemblies 94 are mounted on the tabs 20A and 20B, and 27A and 27B, so that the wires 86 can be restrained. Additionally, the wires 86 can also be passed under the strips 64A and 64B on the ends of the guide members 52A and 52B, and 54A and 54B to provide additional restraint. Additionally, lead wires from eye position and respiration rate sensors, etc. (not shown) could also be secured in a similar manner.

Illustrated in FIGS. 8 and 9 is a second embodiment of the invention wherein, for purposes of explanation, elements similar to those shown in FIGS. 1–7 are identified by the identical number, but having a "prime" added thereto. Here the attachment fitting 10' has a ear attachment fitting 12A', that incorporates a series of tabs: 20A' that include slots 21A' and 96A that extend therethrough; tab 22A'. A first strap 30', is adapted to fit about the forehead 31 of the person's head 18. The strap 30 includes an end portions 34A' that is looped through slots 21A and 96A in the tabs 20A' and back thereon. A pad 38' is bonded to the tab 20A' to which the end portion is secured thereto. A second (rear) strap 42', and sets 50A' and 50B' of guide members are joined to the tabs 24A' and 27A' in an identical fashion.

Still referring to FIG. 8 and additionally to FIGS. 10 and 11, it can be seen that the set 50B' includes guide members 54A' and 54B', to which are mounted electrode mounts 70'. As in the previous example, the individual guide members 54A' and 54B', being deformable in cross-sectional shape ,pass through belt loops 72' on the electrode mounts such that each of the guide members are deformed when passing therethrough. This deformation produces sufficient friction so as to releasably hold the electrode mounts 70' in any set position. The electrode mounts 70 include a centrally located hole in which is mounted commercially available bell shaped electrode 88' having a lead wire 86'. The one edge of the hole 76' incorporates a tab 104 that secures the electrode 88' in place. Additional retention is accomplished by sliding the lead wire 86' through a belt loop 108. Finally, the electrode mount 70', being made of a semi-flexible material, is permanently bent into the shape of a U. Thus when the head set 10' is mounted on the head 18 of a patient, the compression force on the electrode mount 70'; causes the mount to deform biasing the electrode 88' into contact with the head. Note that this U shaped electrode mount 70' could also be used with the electrode mount 70 illustrated in FIGS. 1–7. As shown in FIG. 8, electrodes 88' can also be mounted on the attachment fitting 14A' to provide additional monitoring of brain activity. Here they are positioned to monitor from the mastoid area behind the ear 15.

It is important to note that, while the use of hook and eye type fasteners are illustrated, the head set is not limited to their use. For example, snap type fasteners or button/button holes fasteners could also be used. In addition, the strap and guide member material could be significantly varied, all that is required is that it be flexible and compressible. However, the electrode mounts could be mounted to the guide members by snap type fasteners, or the like, only requiring that the material be flexible. In addition, while it is preferred to have the attachment fittings attach about the ears of the person, it could just as well be attached by other means, such as tape to temples of the patent (not shown).

Thus it can be seen that all the objects of the invention have been achieved. The head set for mounting electrodes for monitoring brain electrical activity is fully adjustable to the head of the person. It allows for the adjustment of the electrode placement. It also does not require restraints to be placed under the chin of the person and only requires minimal coverage of the head of the person when installed. Furthermore, the use of flexible and deformable (compressible) straps and guide members makes the head set more comfortable to wear for long periods. This feature, along with the others previously discussed, make the headset ideally suitable for overnight sleep studies. However, it should be noted that the head set is not limited to sleep studies. The headset can be used for any procedure pertaining to the monitoring and evaluation of brain electrical activity.

While the invention has been described with reference to particular embodiments, it should be understood that the embodiments are merely illustrative as there are numerous variations and modifications which may be made by those skilled in the art. Thus, the invention is to be construed as being limited only by the spirit and scope of the appended claims.

INDUSTRIAL APPLICABILITY

The invention has applicability to any industry where brain electrical activity studies are desired and, in particular to the medical apparatus industry.

I claim:

1. A headset for supporting electrodes used for electrical measurements of the brain of a person comprising:

first and second mounting fittings for attachment about the head of the person;

first and second flexible straps having first and second ends connected to said first and second mounting fittings, respectively, said first and second straps adapted to fit about the forehead and rear of the head of the person;

a plurality of flexible guide members, said guide members having first and second ends connected to said first and second mounting fittings, respectively; and a plurality of electrode mounts movably mounted to said guide members.

2. The headset as set forth in claim 1 wherein said plurality of flexible guide members are in sets of two.

3. The head set as set forth in claim 2 wherein said plurality of sets of guide members are positioned between said first and second straps.

4. The head set as set forth in claim 3 wherein said first and second straps are adjustable in length.

5. The headset as set forth in claim 4 wherein said each of said flexible guide members of said flexible members in said sets of two are adjustable in length.

6. The head set as set forth in claim 5 wherein electrodes are removably mounted in said electrode mounts.

7. The head set as set forth in claim 6 wherein said electrode mounts include means to bias the electrodes toward the head of the person when the head set is installed on the head of the person.

8. The headset as forth in claim 7 where in said means to bias the electrodes toward the head of the person includes each electrode mount being made of a semi-flexible material and is formed in a generally U shape with the electrode mounted in the middle of the U shaped portion.

9. The headset as set forth in claim 8 comprising said plurality of sets of guide members in a generally parallel relationship with each other and each of said guide members of each of said sets in a parallel spaced relationship to each other.

10. The headset as set forth in claim 8 comprising:

said electrode mounts have belt loops in a spaced relationship; each of said guide members of said plurality of sets of guide members being de-formable in cross-sectional shape and passing through said belt loops such that each of said guide members are deformed when passing there through producing sufficient friction as to releasably hold said electrode mounts in position.

11. The head set as set forth in claim 10, comprising:

said electrodes having lead wires attached thereto; and a flexible wire harness detachably mounted to said second strap adapted to receive said wires.

12. The headset as set forth in claim 11 comprising:

said first and second mounting fittings having a plurality of openings;

said first and second ends of said first and second straps and each of said guide members having first and second ends, said first and second ends looped through one of said openings of said first and second mounting fittings, respectively; and fastener means mounted on said first and second ends of said first and second straps and said guide members, said fastener means for releasably securing said straps and said guide members to said first and second mounting fittings.

13. The head set as set forth in claim 12 wherein said fastener means are hook and eye type fasteners.

14. The headset as set forth in claim 1, or 2, or 3, or 4, or 5, or 6, or 7, or 8, or 9, or 10, or 11, or 12, or 13 wherein said mounting fittings are adapted to attach to the head of the person about the ears thereof.

15. The head set as set forth in claim 14 wherein said first and second straps and said guide members comprise:

a compressible foam core; and cover sheets made of a flexible material having a nap suitable for acting as a eye portion of a hook and eye type fastener.

16. A head set for supporting electrodes used for measuring the electrical activity of the brain of a person comprising:

first and second mounting fittings for attachment about the ears of a person;

first and second flexible straps having first and second ends connected to said first and second mounting fittings, respectively, said first and second straps adapted to fit about the forehead and rear of the head of the person, respectively;

a plurality of sets of flexible guide members, said guide members having first and second ends connected to said first and second mounting fittings, respectively; and a plurality of electrode mounts, having electrodes for monitoring brain activity mounted therein, movably mounted to each of said plurality of sets of flexible guide members.

17. The head set as set forth in claim 16 comprising friction means coupling said electrode mounts to said sets of guide members.

18. The head set as set forth in claim 17 wherein said first and second straps, and said guide members are adjustable in length.

19. The headset as forth in claim 18 wherein said electrode mounts include means to bias said electrodes toward the head of the person and each electrode mount being made of a semi-flexible material and is formed in a generally U shape with the electrode mounted in the middle of the U shaped portion.

20. The headset as set forth in claim 19 wherein said straps and said guide members comprise:

a flexible and compressible foam core; and flexible cover sheets joined to either side of said foam cores.

21. The head set as set forth in claim 20 wherein said guide members have specific cross-sectional areas and the head set includes means to releasably secure said electrode mounts to said sets of guide members comprising:

belt loops in a spaced relationship having a smaller cross-sectional area than said guide members; and said individual guide members passing through said belt loops such that each of said guide members are deformed when passing therethrough producing sufficient friction as to releasably hold said electrode mounts in position.

22. The headset as set forth in claim 16, or 17, or 18, or 19, or 20, or 21 comprising:

electrical wires connected to said electrodes;

a flexible wire harness coupled to said second strap for receiving said wires; and means to secure said electrical wires to the headset from said electrode mounts to said wire harness, such that said wires are prevented from moving away from the head of a person.

* * * * *